US011460476B2

(12) United States Patent
Kauffmann et al.

(10) Patent No.: US 11,460,476 B2
(45) Date of Patent: Oct. 4, 2022

(54) DYE-BASED LIQUID REAGENT VOLUME INDICATOR FOR USE IN ANALYTE DETECTION ASSAYS

(71) Applicant: Siemens Healthcare Diagnostics Inc., Tarrytown, NY (US)

(72) Inventors: Aaron Kauffmann, Elkhart, IN (US); David Ledden, Elkhart, IN (US); Chris Zimmerle, Goshen, IN (US); Jon Stradinger, Kalamazoo, MI (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/435,433

(22) PCT Filed: Feb. 26, 2020

(86) PCT No.: PCT/US2020/019835
§ 371 (c)(1),
(2) Date: Sep. 1, 2021

(87) PCT Pub. No.: WO2020/180552
PCT Pub. Date: Sep. 10, 2020

(65) Prior Publication Data
US 2022/0043010 A1    Feb. 10, 2022

Related U.S. Application Data

(60) Provisional application No. 62/813,289, filed on Mar. 4, 2019.

(51) Int. Cl.
*G01N 33/72* (2006.01)
*G01N 33/49* (2006.01)
(Continued)

(52) U.S. Cl.
CPC ......... *G01N 33/723* (2013.01); *G01N 33/583* (2013.01); *G01N 33/726* (2013.01);
(Continued)

(58) Field of Classification Search
CPC .... G01N 33/48; G01N 33/483; G01N 33/487; G01N 33/49; G01N 33/52; G01N 33/583;
(Continued)

(56) References Cited

U.S. PATENT DOCUMENTS 5,162,237 A * 11/1992 Messenger ............... B01L 3/502
                                                        422/417
5,272,093 A * 12/1993 Silva ....................... B01L 3/505
                                                        206/569
(Continued)

FOREIGN PATENT DOCUMENTS

| JP | 2000061448 A | 2/2000 |
| KR | 960042054 A | 12/1996 |
| WO | 2018/017332 A1 * | 1/2018 |

OTHER PUBLICATIONS

International Search Report and Written Opinion of International Application No. PCT/US2020/019835 dated May 21, 2020.

*Primary Examiner* — Maureen Wallenhorst

(57) ABSTRACT

Devices, kits, and methods are disclosed for use in detecting a concentration of an analyte of interest in a patient's liquid test sample. The devices, kits, and methods employ the use of one or more solid reagent zones that includes at least one analytical reagent for detection of an analyte of interest. The solid reagent zone(s) also includes at least one dye for determining whether results obtained from the diagnostic assay for the at least one analyte of interest are biased or inaccurate due to a loss of volume of a liquid reagent during the dispensing of the liquid reagent.

20 Claims, 10 Drawing Sheets

(51) Int. Cl.
    *G01N 33/58* (2006.01)
    *B01L 3/00* (2006.01)
(52) U.S. Cl.
    CPC .............. *B01L 3/502* (2013.01); *B01L 3/5027* (2013.01); *G01N 33/49* (2013.01); *G01N 2440/38* (2013.01)
(58) Field of Classification Search
    CPC .. G01N 33/721; G01N 33/723; G01N 33/726; G01N 2440/38; G01N 21/314; B01L 3/00; B01L 3/502; B01L 3/5027
    USPC ...... 436/63, 66, 67, 164, 165; 422/401, 402, 422/408, 415, 419, 430, 82.05, 82.09, 422/502, 506
    See application file for complete search history.

(56) References Cited

U.S. PATENT DOCUMENTS

| | | | |
|---|---|---|---|
| 5,372,948 A * | 12/1994 | Yip | B01L 3/502 422/417 |
| 5,637,505 A | 6/1997 | Li et al. | |
| 5,891,730 A | 4/1999 | Li et al. | |
| 2007/0141696 A1 | 6/2007 | Baugh et al. | |
| 2009/0093012 A1* | 4/2009 | Bae | G01N 33/726 435/29 |
| 2013/0084592 A1 | 4/2013 | Seiple | |
| 2015/0000428 A1 | 1/2015 | Fukuda et al. | |
| 2015/0044764 A1* | 2/2015 | Cha | A61B 5/150343 435/288.7 |
| 2018/0193842 A1* | 7/2018 | Liu | G01N 33/53 |
| 2020/0368746 A1* | 11/2020 | Kauffmann | B01L 3/502715 |

\* cited by examiner

DYE-BASED LIQUID REAGENT VOLUME INDICATOR FOR USE IN ANALYTE DETECTION ASSAYS

This application claims priority to U.S. provisional application No. 62/813,289, filed Mar. 4, 2019, the disclosure of which is incorporated herein by reference in its entirety.

STATEMENT REGARDING FEDERALLY FUNDED RESEARCH OR DEVELOPMENT

Not Applicable.

TECHNICAL FIELD

The presently disclosed and claimed inventive concept(s) relate to a device(s), kit(s), and method(s) that dispense at least one liquid, including, but not limited to, at least one liquid reagent(s) and/or buffer, for the conductance of at least one diagnostic assay. More specifically, the presently disclosed and claimed inventive concept(s) relate to non-limiting embodiments of a modified reaction cassette that comprises at least one dye for determining whether the results obtained from the conductance of at least diagnostic assay are biased, as well as kits and methods of use related thereto.

BACKGROUND

Numerous devices and methods exist for detecting analytes that may be present in a fluid sample. Such devices have been proven to be effective in diagnostic assays that detect the presence and quantity of certain analytes indicative of a patient's health, including, but not limited to, glycated hemoglobin (HbA1c), microalbumin and creatinine, and lipid-based analytes, such as cholesterol, triglycerides, and/or high-density lipoproteins. However, the results obtained from the conductance of such analyte detection assay(s) may be inaccurate and/or biased due to, for instance, increased reagent concentration(s) resulting from incomplete evacuation of assay buffer(s) from a buffer tray contained within a reaction vessel, such as, by way of example, a diagnostic assay reaction cassette for use within a diagnostic assay analyzer. In addition, inaccuracies and biases can be introduced due to the loss of assay buffer from the buffer tray, such loss being caused by, for example, the assay buffer adhering to a pull tab of the buffer tray. When the tab is pulled by a user to release the buffer(s) from the buffer tray into the reaction vessel, a portion of the assay buffer(s) may adhere to the tab and be subsequently removed from the reaction vessel when the tab is removed from the buffer tray by the user. As a result, the predetermined volume of assay buffer(s) is not delivered to the reaction vessel resulting in the increased concentration(s) of the diagnostic assay reagent(s) causing the results of the diagnostic assay(s) to be biased. In addition, the repeated bias of individual diagnostic assays/tests increases the coefficient of variation (% CV) obtained from the collective dataset, thereby decreasing the accuracy and repeatability of the diagnostic assay(s).

While a number of solutions have been proposed to ensure complete delivery of assay buffer(s) within a diagnostic assay system, including, for instance, user instructions to pull the tab firmly and slowly, automated puncturing of the buffer tray/pouch, and centrifugation of the buffer, such proposed solutions require additional time-consuming steps and/or are subject to user-introduced error(s). Accordingly, there is a need for improved devices and methods that are capable of detecting variations from pre-determined volume(s) of assay buffer(s) utilized in the conductance of one or more diagnostic assays to thereby mitigate or eliminate biases and/or inaccuracies in assay results associated with such variations. It is to such devices and methods, as well as kits related thereto, that the presently disclosed and claimed inventive concept(s) is directed.

DETAILED DESCRIPTION

Figure 1:
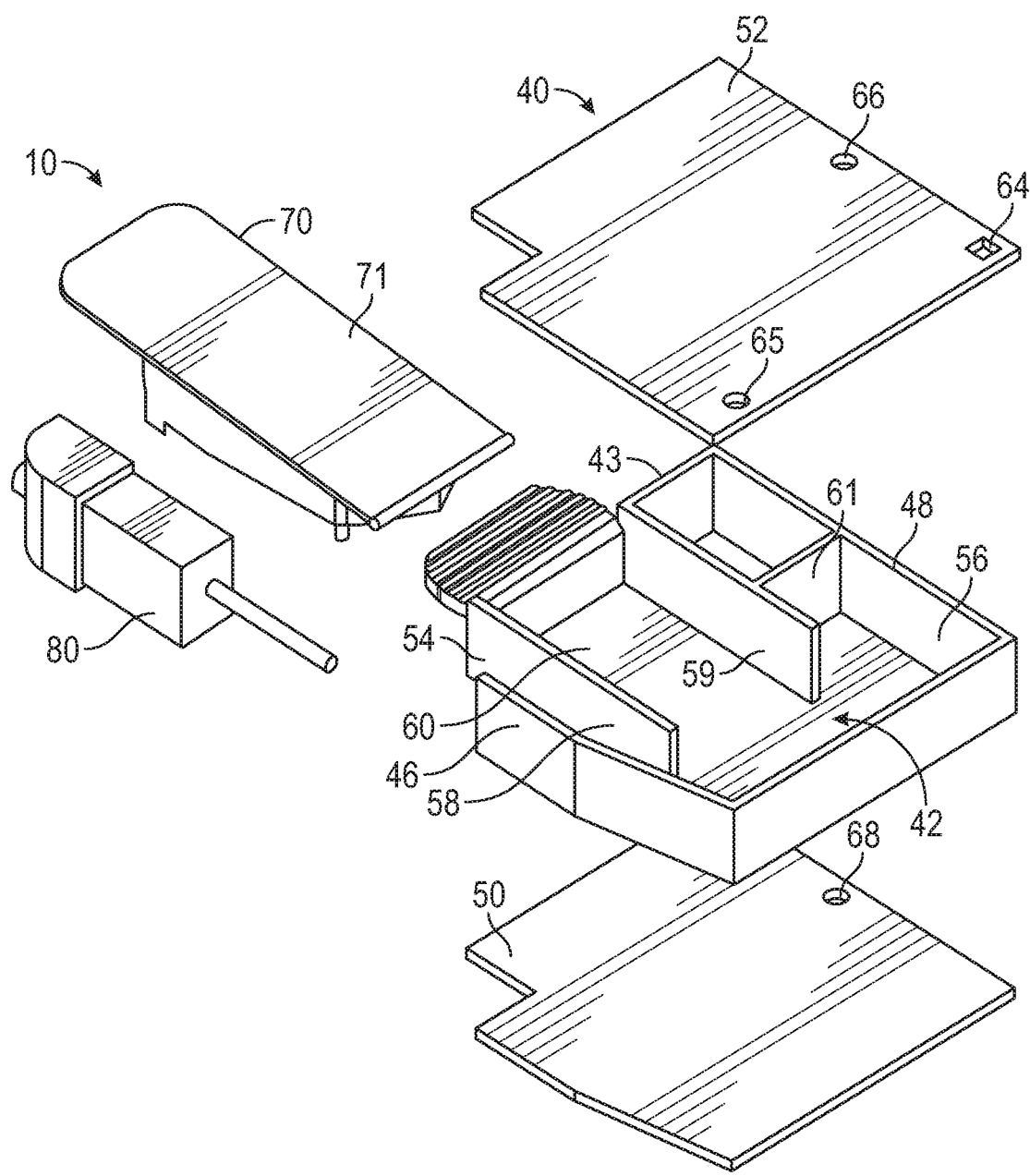
FIG. 1 is an exploded of one embodiment of an analytical reaction kit constructed in accordance with the presently disclosed and/or claimed inventive concept(s).

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "dye(s)" as used herein will be understood to include any dye commonly known in the art that exhibits known absorption(s) of light at various wavelengths, for instance, by way of example only, within the infrared spectrum, such as from about 700 nanometers to about 900 nanometers. Dye(s) capable of being utilized in accordance with the presently claimed and/or inventive concept(s) include, by way of example only, naphthol green B (NGB), 1,1',3,3,3',3'-hexamethyllindotricarbocyanine iodide, 1,1'-diethyl-4,4'-carbocyanine iodide, manganese (II) pthalocyanine, silicon 2,3-napthalocyanine dichloride, 3,3'-diethylthiatricarbocyanine perchlorate, near infrared (NIR)-II dye carboxylic functionalized, and combinations thereof. In addition, any combination of iodide-based dyes, phthalocyanine-based dyes, and/or infrared dyes commonly known in the art can be used in accordance with the presently disclosed and/or claimed inventive concept(s).

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

Turning now to particular embodiments, the presently disclosed and claimed inventive concept(s) relate to a device(s), kit(s), and method(s) for dispensing at least two liquid reagents for use in analyte(s) detection assays. More specifically, the presently disclosed and claimed inventive concept(s) relate to a modified apparatus present within a reaction cassette that is capable of dispensing at least two liquid reagents for use in analyte(s) detection assays, as well as kits and methods of use related thereto.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radio-immunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radio-immunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any fluid sample, including, without limitation, whole blood, plasma, serum, or urine.

Referring now to FIG. 1, shown therein is a non-limiting embodiment of a detailed, exploded view of an analytical research kit 10 constructed in accordance with the presently disclosed and/or claimed inventive concept(s). The analytical research kit 10 comprises a reaction cassette 40, a liquid reagent container 70, and a capillary 80, which may be utilized both for obtaining a liquid test sample from a patient and introducing such sample into the reaction cassette 40.

The reaction cassette 40 comprises a body 42 formed by the top perimeter side 43, a bottom perimeter side 44, a first perimeter side 46, a second perimeter side 48, and a bottom portion 50. The reaction cassette 40 further comprises a top portion 52 that is used to seal the body 42 of the reaction cassette 40 after the liquid reagent container 70 containing the diagnostic assay buffer(s) and/or liquid assay reagent(s) has been incorporated into the reaction cassette 40 as described and/or claimed herein. Such seal can be accomplished via any method commonly known in the art, including, without limitation, adhesive(s), glue, sonic welding, laser welding, and/or any permanent fastener(s).

In one embodiment, the body 42 of the reaction cassette 40 is constructed such that the body is formed via the connection of the top perimeter side 43, the bottom perimeter side 44, the first perimeter side 46, and the second perimeter side 48 to the bottom portion 50. Such connection can be via any method commonly known in the art, including, without limitation, adhesive(s), glue, sonic welding, laser welding, and/or any permanent fastener(s). In another embodiment, the body 42 can be constructed such that the top perimeter side 43, the bottom perimeter side 44, the first perimeter side 46, the second perimeter side 48, and the bottom portion 50 is one contiguous piece, for instance, by way of example only, one contiguous piece of plastic.

The reaction cassette 40 has a substantially horizontal axis of rotation. While the external dimensions of the reaction cassette 40 are not critical, the reaction cassette 40 typically has a height and width of about 3 centimeters to about 15 centimeters and a thickness of about 0.25 centimeters to about 2 centimeters. In one embodiment, the dimensions of the reaction cassette 40 are a height and width of about 6 centimeters and a thickness of about 1 centimeter.

The body 42 of the reaction cassette 40 further comprises a first inner wall 58 and a second inner wall 59, wherein the first inner wall 58 and the second inner wall 59 extend downward from the top perimeter wall 43 and are positioned opposite of one another and substantially perpendicular to the top perimeter wall 43 and the bottom perimeter wall 44. The first perimeter side 46, together with the second perimeter side 48, the bottom portion 50, and the top portion 52 form a reaction chamber 56, a portion of which is U-shaped and formed by a third inner wall 61 which extends between and substantially perpendicular to the second inner wall 59 and the second perimeter side 48. Once the body 42 of the reaction cassette 40 has been sealed by the top portion 52 following the incorporation of the liquid reagent container 70 into the reaction cassette 40, an inlet 54 is thereby formed between the first perimeter side 46 and the first side wall 58, the inlet 54 being substantially parallel to the first perimeter side 46 and the first side wall 58 and extending from the top perimeter side 43 downward toward the bottom perimeter side 44 of the reaction cassette 40. The inlet 54 is capable of securely receiving the capillary 80 such that the liquid test sample (not shown) is introduced from the capillary 80 into the reaction chamber 56 of the reaction cassette 40. While a capillary 80 is shown in the Figures as introducing the liquid test sample (not shown) into the reaction chamber 56 of the reaction cassette 40, it should be readily understood to a person having ordinary skill in the art that the liquid test sample (not shown) can be introduced into the reaction cassette 40 via any device capable of introducing a liquid a test sample, including, by way of example and not by way of limitation, a pipette(s). In addition, the inlet 54 can be stoppered, plugged, or otherwise closed subsequent to the introduction of the liquid test sample into the reaction cassette 40 so as to prevent liquid loss during the course of the methodologies described herein, including, but not limited to, assays, including immunoassays.

With specific reference to the liquid reagent container 70, while the figures depict embodiments of the liquid reagent container 70 as comprising at least one cavity 75 (shown in FIG. 2), it should be readily understood to a person having ordinary skill in the art that the liquid reagent container 70 may be comprised of any number of cavities. By way of example and not by way of limitation, the liquid reagent container 70 may comprise 1, 2, 3, 4, 5, 6, 7, 8, 9, 10, 15, 20, 25, 50 or any number of cavities capable of being manufactured for incorporation in liquid reagent container 70. As shown in FIG. 1, the liquid reagent container 70 comprises a flexible cover 71. The flexible cover 71 is removably affixed to the liquid reagent container 70 to seal the container and the at least one cavity 75, thereby sealing in and preventing the discharge of the at least one liquid reagent from the at least one cavity 75 of the container 70. When the liquid reagent container 70 is oriented in a substantially vertical position (as shown in greater detail in FIG. 2) within the reaction cassette 40, the flexible cover 71 can be removed by a user to allow for the gravitational dispensing of the at least one liquid reagent/buffer from the at least one cavity 75. In one non-limiting embodiment, the liquid reagent container 70 is fabricated as a molded component formed of a rigid plastic material (so as to avoid deformation of the container 70 upon removal of the flexible cover 71 therefrom by a user), including, for example, high-density polyethylene; however, the container 70 may be constructed of any material capable of accomplishing the presently disclosed and/or claimed inventive concept(s). The flexible cover 71 may be, by way of example only, constructed of a vapor and liquid impermeable material, including, for example, a plastic laminate material or aluminum foil material. In one embodiment, the flexible cover 71 is affixed to the container 70 by a heat-activated peelable adhesive that leaves substantially no residue on the container 70 when the flexible cover 71 is removed by a user. In one embodiment, the flexible cover 70 may be constructed and configured to comprise a pull tab portion, which can be grasped and pulled by a user to remove the flexible cover 71 from the reaction cassette 70.

Figure 2:
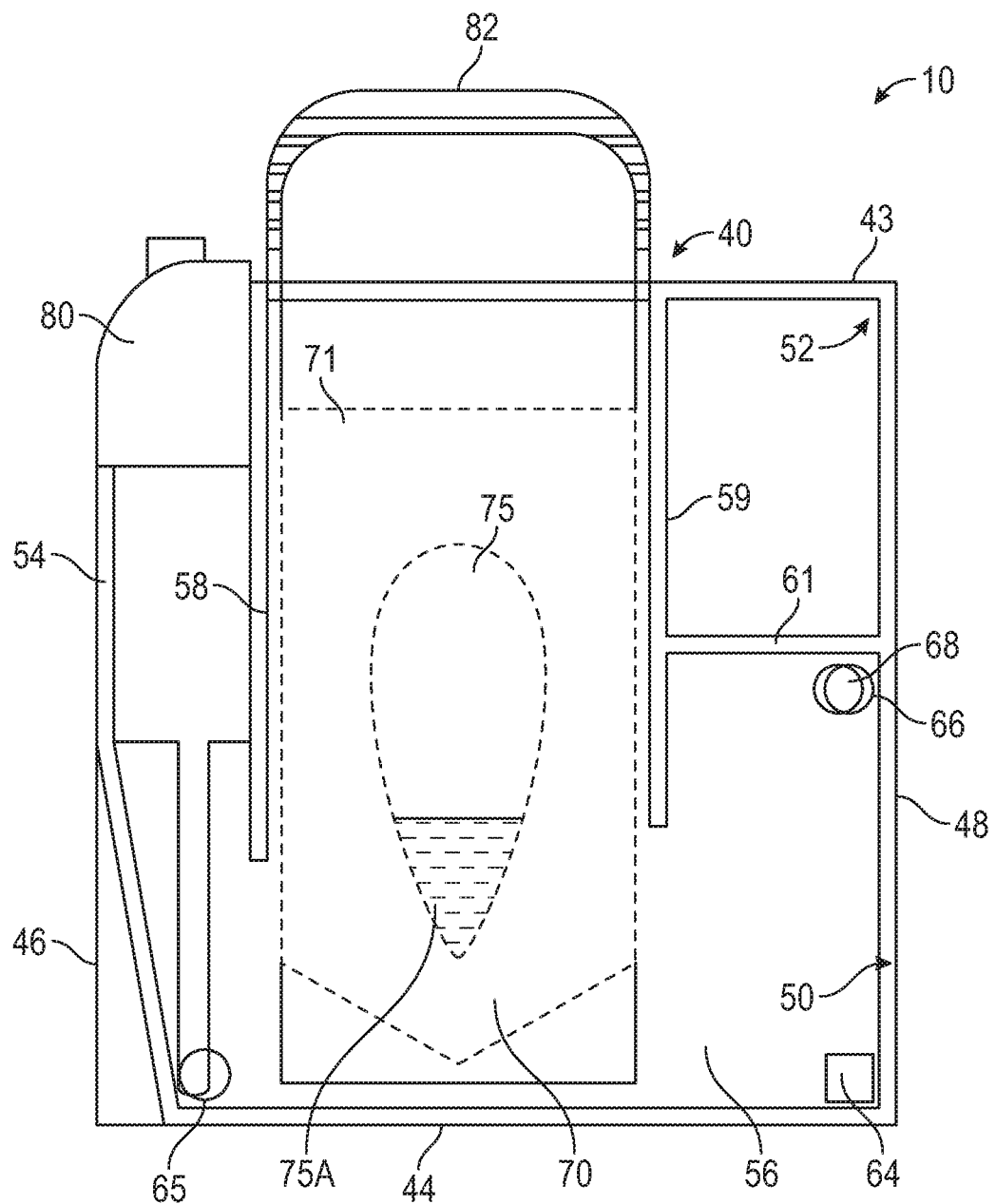
FIG. 2 is a top view of one embodiment of an analytical reaction kit constructed in accordance with the presently disclosed and/or claimed inventive concept(s).

Referring now to FIG. 2, shown therein is one non-limiting embodiment of the analytical reaction kit 10 which comprises a liquid reagent container 70 which has been incorporated into a reaction cassette 40 and the capillary 80 which has been securely received into the inlet 54 of the reaction cassette 40. As shown in the FIG. 2, the liquid reagent container 70 remains closed and sealed by the flexible cover 71 thereby sealing in the liquid reagent/buffer 75A within the cavity 75. In one non-limiting embodiment, the liquid reagent container 70 is affixed within the reaction cassette 40 whereby the container 70 is positioned so as to secure between the first inner wall 58 and the second inner wall 59. The first perimeter side 46, together with the second perimeter side 48, the bottom portion 50, and the top portion 52 form a reaction chamber 56, a portion of which is U-shaped and formed by a third inner wall 61 which extends between and substantially perpendicular to the second inner wall 59 and the second perimeter side 48. The reaction chamber 56 is in fluid communication with the inlet 54, thereby allowing a liquid test sample (not shown) to be introduced via the capillary 80 into the reaction chamber 56 of the reaction cassette 40.

In one embodiment and as shown in FIG. 2, positioned along the reaction chamber 56 is a sample read window 64, a first solid reagent zone 65, a second solid reagent zone 66, and a third solid reagent zone 68. While shown in the Figures as comprising three individual solid reagent zones, it should be understood to a person having ordinary skill in the art, that any number of solid reagent zones may be used (or may be totally absent from reaction cassette 40) and positioned at any location(s) along the reaction chamber 56 in order to accomplish the presently disclosed and/or claimed inventive concept(s). The sample read window 64 can be, by way of example only and not by way of limitation, a transparent cuvette window or an optical window which permits the accurate measurement of detectable signals in the area of the sample read window 64. In one embodiment, the first solid reagent zone 65 is substantially located at a corner of the reaction cassette 40 formed from the perpendicular intersection of the first perimeter wall 46 and the bottom perimeter wall 44 wherein the first solid reagent zone 65 is formed on the top portion 52 of the reaction cassette 41. In one embodiment, the second solid reagent zone 66 and the third solid reagent zone 68 are substantially located at a corner of the reaction cassette 41 formed from the perpendicular intersection of the second perimeter wall 48 and the third inner wall 61 wherein the second solid reagent zone 66 is formed on the top portion 52 of the reaction cassette 41 and the third solid reagent zone 68 is formed on the bottom portion 50 of the reaction cassette 41. When present, the solid reagent zones 65, 66, and 68 are incorporated with solid analytical reagents for performing a particular analytical assay procedure. The solid analytical reagents are, in one embodiment, present in the solid reagent zones in a substantially dry, water soluble, suspendable or dissolvable form, and can be incorporated along the reaction chamber 56 according to methods known in the art, such as, for example, by noncovalent binding techniques, absorptive techniques, and the like, in the desired order in which they are to be sequentially contacted with a liquid test sample. In one embodiment, the solid reagent zones 65, 66, and 68, when present, are defined in the form of substantially flat, raised portions or mesa-shaped nodes on the surface of the selected area of the reaction chamber 56, in which the raised upper surface of each node is from about 0.005 inches to about 0.02 inches elevated above a surface of the reaction chamber 56.

In one non-limiting embodiment of the presently disclosed and/or claimed inventive concept(s), the first solid reaction zone 65 comprises an oxidant (such as, for example, ferricyanide) which, as described in further detail hereinbelow, may be formulated, manufactured, and/or combined with at least one dye, the at least one dye having a known extinction coefficient when interrogated by particular wavelength(s) of light.

The second solid reaction zone 66 and the third solid reaction zone 68 comprise an agglutinator and an antibody-latex (for instance, by way of example only, a glycated hemoglobin A1c antibody), respectively. However, it should be readily understood to a person having ordinary skill in the art, that any compound, composition, and/or molecule can be used on the solid reagent zones in order to accomplish the presently disclosed and/or claimed inventive concept(s), including, without limitation, detection of at least one analyte(s) of interest present in a liquid test sample. In addition, it should be understood to a person having ordinary skill in the art that the presently disclosed and/or claimed inventive concept(s) can be accomplished in the absence of any or all of the first solid reagent zone 65, the second solid reagent zone 66, and the third solid reagent zone 68. In such an instance, the at least one liquid reagent/buffer 75A is capable of detecting at least one analyte(s) present in a liquid test sample in the absence of one or all of the solid reagent zones 65, 66, and/or 68.

Figure 3A:
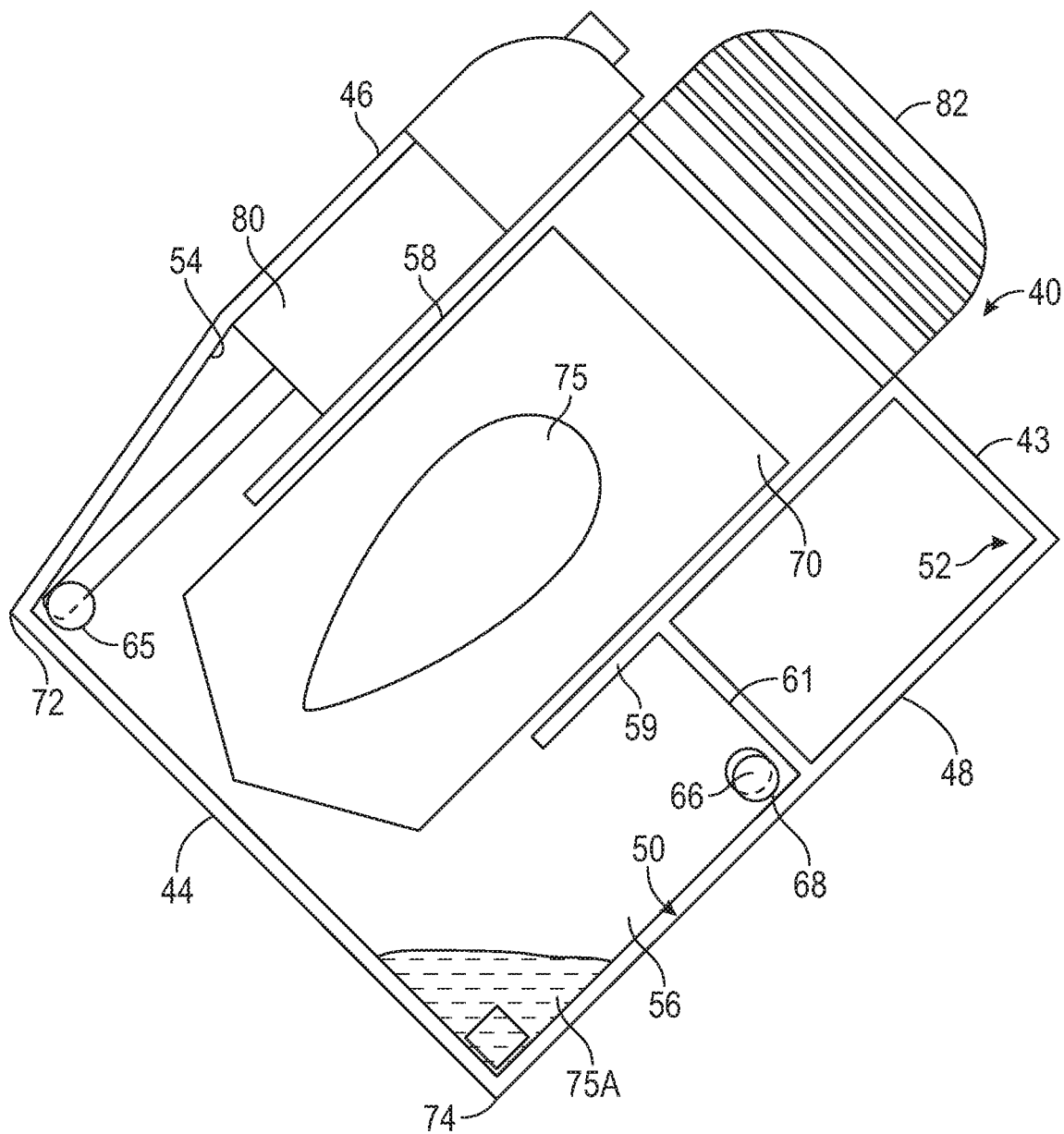
FIGS. 3A-3C are top views of an embodiment of the analytical reaction kit being used for the detection of at least one analyte present in a liquid test sample in accordance with the methodologies disclosed and/or claimed herein.
Figure 3B:
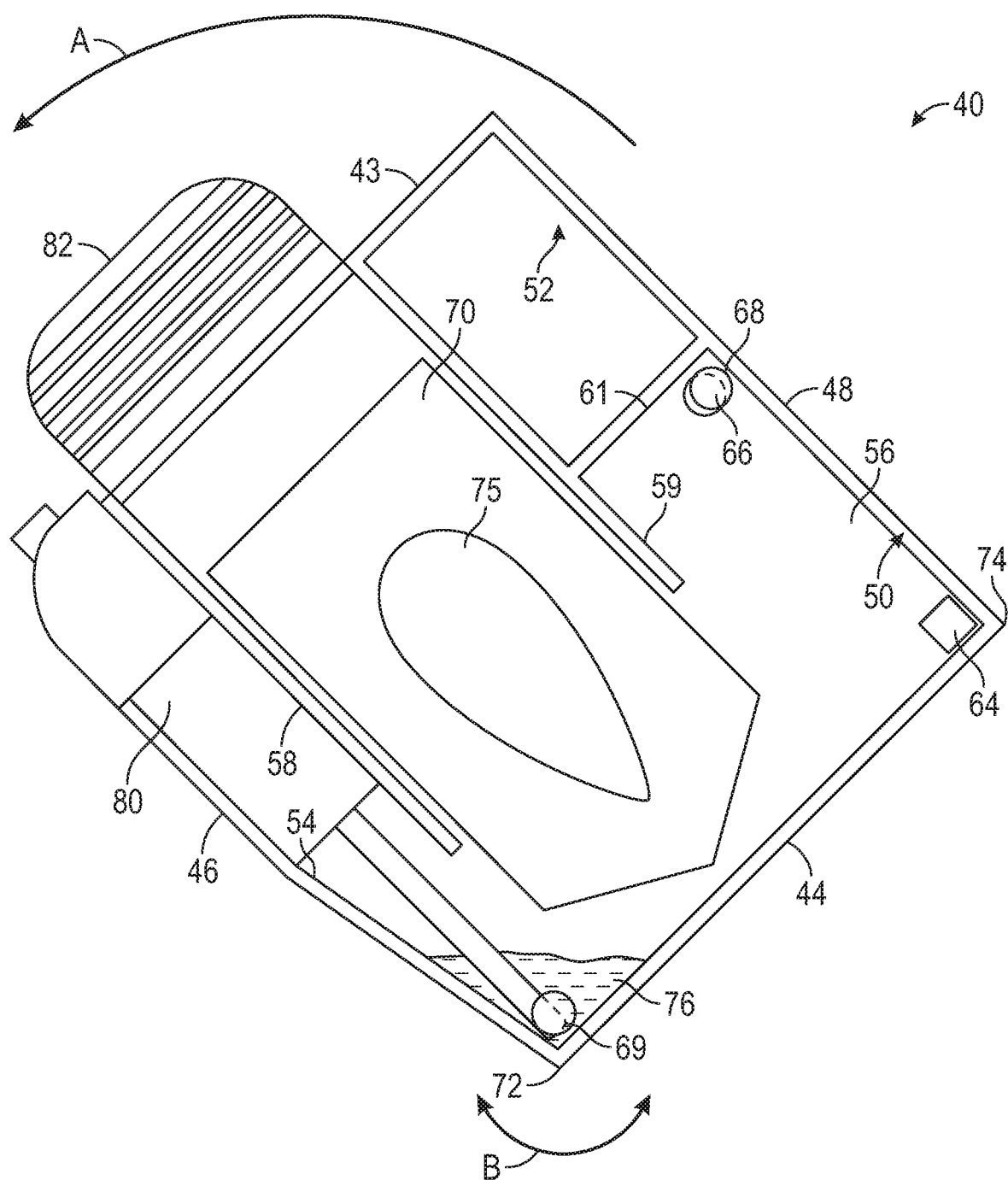
Figure 3C:
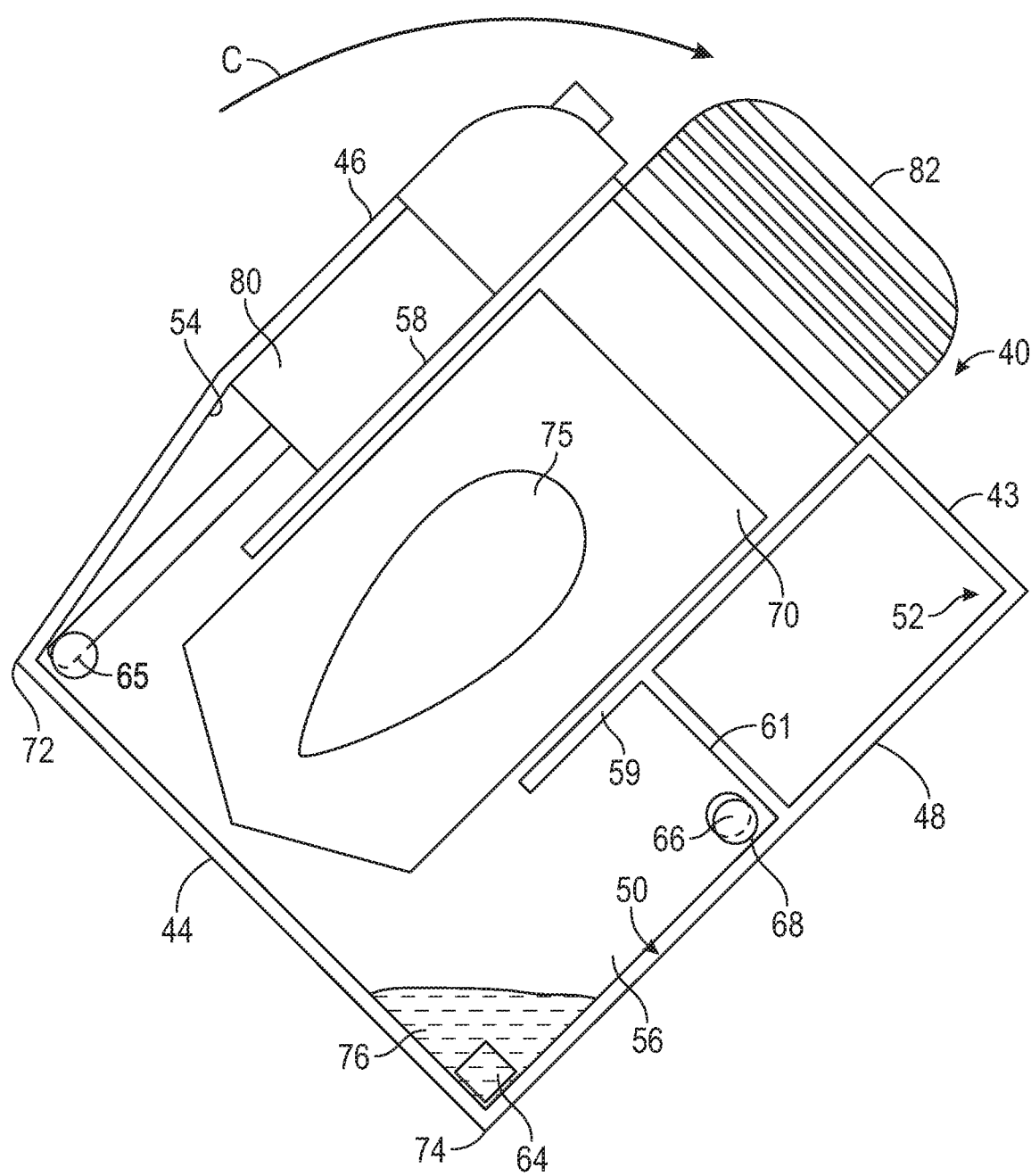

Referring now to FIGS. 3A-3C, shown therein is one embodiment of an analytical reaction cassette 40 constructed in accordance with the presently disclosed and/or claimed inventive concept(s) being used in a method of the presently disclosed and/or claimed inventive concept(s) to detect at least one analyte(s) of interest present in a liquid test sample. While FIGS. 3A-3C show a first solid reagent zone 65, a second solid reagent zone 66, and a third solid reagent zone 68, as described above, and the liquid reagent/buffer 75A, a person having reasonable skill in the art should readily understand that the presently disclosed and/or claimed methodology(-ies) may be accomplished via a combination of any number of solid reagents (present on solid reagent zones) and liquid reagents. The reaction cassette 40 is shown in various rotational positions to further illustrate the gravitational flow and mixing of the liquid test sample (not shown), the liquid reagent/buffer 75A and the first solid reagent zone 65, the second solid reagent zone 66, and the third solid reagent zone 68 along the reaction chamber 56 as the reaction cassette 40 is rotated about a substantially horizontal axis. The solid arrows shown outside of the reaction cassette 40 indicate the direction of rotation of the reaction cassette 40 about the horizontal axis.

It is to be understood that FIGS. 3A-3C are for purposes of illustration only and are not intended to limit the number, nature, or manner of incorporation of analytical reagents (solid and/or liquid) into the reaction cassette 40, or the sequence or direction of rotation of the reaction cassette 40. For example, and as described hereinabove, although three solid assay reagent zones 65, 66, and 68 and the at least one liquid reagent/buffer cavity 75 of the liquid reagent container 70 are shown, other assay procedures, including, but not limited to immunoassays procedures, and, more specifically, immunoturbidimetric assay procedures, can also be performed in the reaction cassette 40 in which the number of analytical reagents (solid and/or liquid) may vary depending on the particular assay requirements. In addition, the reaction cassette 40 may include less than the required number of analytical reagents (solid and/or liquid) for performing an analytical assay procedure where one or more reaction mixtures thereof can first be performed outside of the reaction cassette 40 and then introduced into the reaction cassette 40 to complete the assay.

An illustrative, non-limiting method of using the reaction cassette 40 depicted in FIGS. 1 and 2 will now be described as shown in and with reference to FIGS. 3A-3C. As shown in these Figures, the flexible cover 71 has been removed, thereby allowing the gravitational dispensing and flow of the liquid reagent/buffer 75A from the at least one liquid reagent/buffer cavity 75 into the reaction chamber 56. However, it should be understood to a person having ordinary skill in the art that the flexible cover 71 is present upon insertion of the reaction cassette 40 into the suitable instrument, apparatus, or system and is selectively removed at the appropriate time (as described below) by a user during the conductance of the at least one assay test. As discussed herein, the various rotation and oscillation movements of the reaction cassette 40 can be performed manually, but in most cases will be performed by a suitable instrument, apparatus, or system, including, without limitation, the DCA Vantage® Analyzer commercially available from Siemens Healthcare Diagnostics, Inc.

In one embodiment, the first step is to provide the reaction cassette 40 into a holder mechanism of the above-referenced instrument, apparatus, or system such that a second corner 74 of the reaction cassette 40, which is formed by the substantial perpendicular intersection of the second perimeter side 48 and the bottom perimeter side 44, is positioned in a downward orientation. Following insertion of the reaction cassette 40 into the suitable instrument, apparatus, or system, a liquid test sample (not shown) is drawn into the capillary 80 and the capillary 80 containing the liquid test sample is inserted into inlet 54 whereby the liquid test sample contained in the capillary 80 is proximally located near a first corner 72 of the reaction cassette 40. Upon insertion of the capillary 80 into the inlet 54 of the reaction cassette 40, the capillary 80 seals the inlet 54 of the reaction cassette 40. The portion of the capillary 80 near the first corner 72 is preferably configured as shown such that when the capillary 80 is positioned as described above, the portion of the capillary 80 containing the liquid test sample is capable of being efficiently contacted by a liquid in the reaction chamber 56, such as the liquid reagent/buffer 75 introduced into the reaction chamber 56 from the at least one cavity 75 of the liquid reagent container 70.

As shown in FIG. 3A, the liquid reagent/buffer 75A contained within the at least one cavity 75 is introduced into the reaction chamber 56 by pulling the pull tab portion of the flexible cover 71 in a direction away from the reaction cassette 40. The liquid reagent/buffer 75A (which, for example, may be a non-reactive buffer solution) is freely dispensed and flows by gravity into the second corner 74 of the reaction chamber 56. A blank absorbance reading can be taken through the sample read window 64 as the starting position with the second corner 74 oriented downward.

As shown in FIG. 3B, the reaction cassette 40 may then be rotated in a counter-clockwise direction (as shown by solid directional arrow A) and oscillated (as shown by solid arrow B) whereby the liquid reagent/buffer 75A is transported by gravity along the reaction chamber 56 from the second corner 74 and brought into contact with the first corner 72 and the portion of the capillary 80 containing the liquid test sample (not shown). It is to be understood that, in accordance with the presently disclosed and/or claimed inventive concept(s), the turbulence caused by the liquid reagent/buffer 75A impacting the first corner 72 during oscillation of the reaction cassette 40 results in the removal of the liquid test sample from the capillary 80 to form a first reaction mixture 76. In addition, in the presence of the first solid reagent zone 65, the oscillation allows for the solubilization of the at least one solid analytical reagent and/or dye present on the first solid reagent zone 65 by the liquid reagent/buffer 75A. The reaction cassette 40 can be maintained in a stationary position for a predetermined amount of time to allow the at least one analyte(s) present in the first reaction mixture 76 to sufficiently interact and/or associate with the first liquid reagent/buffer 75A and/or the solid analytical reagent and/or at least one dye.

As previously discussed, in one non-limiting embodiment the first solid reaction zone 65 comprises an oxidant (such as, for example, ferricyanide) which, is formulated, manufactured, and/or combined with at least one dye, the at least one dye having a known extinction coefficient when interrogated by particular wavelength(s) of light. In one non-limiting embodiment, the known extinction coefficient is measured at a particular wavelength or range of wavelengths of light, for instance, by way of example only, from about 530 nanometers to about 540 nanometers and for wavelengths within the infrared spectrum of from about 700 nanometers to about 900 nanometers.

The dye is utilized as an indicator of the actual volume of the liquid reagent/buffer 75A that is dispensed from the at least one cavity 75 of the liquid reagent container 70. As previously mentioned, when a user selectively removes the flexible cover 71 from the liquid reagent container 70 to release the liquid reagent/buffer 75A into the reaction chamber 56, a portion of the liquid reagent/buffer 75A may remain adhered to and/or associated with the adhesive portion of the flexible cover 71. Accordingly, when the flexible cover 71 is removed, the volume of liquid reagent/ buffer 75A remaining on the flexible cover 71 is likewise removed, thereby resulting in a decrease in the predetermined amount of the liquid reagent/buffer 75A being delivered into the reaction chamber 56. When this happens, the concentrations of the solid and/or liquid reagents (for instance, the one or more solid reagents present in or on the node(s) of the first reagent zone 65, the second reagent zone 66, and/or the third reagents zone 68) are increased causing the results of the test(s) to be biased. The increased bias of individual tests increases the coefficient of variation (% CV) (measured as the ratio of the standard deviation of the dataset to the mean of the dataset) of the collective dataset, resulting in the imprecision and unrepeatability of the assay(s) performed.

In one non-limiting embodiment of the presently disclosed and/or claimed inventive concept(s), the dye (for instance, by way of example only, Naphthol Green B (NGB)) is dried down with the oxidant (for instance, by way of example only, ferricyanide (FeCN)) on the node(s) comprising the first solid reagent zone 65. Following the blank absorbance reading of the liquid reagent/buffer 75A being taken in the sample read window 64 (as shown in FIG. 3A), the reaction cassette 40 is rotated (as shown in FIG. 3B) such that the liquid reagent/buffer 75A rinses and/or solubilizes the patient's liquid test sample (for instance, whole blood), oxidant, and dye to form the first reaction mixture 76.

Where the first reaction mixture 76 provides one or more detectable responses or measureable characteristics (for instance, by way of example only, a first absorbance and a second absorbance) which is required or desired to be measured according to a particular assay protocol, as shown in FIG. 3C, the reaction cassette 40 is rotated in a clockwise direction (as shown by the solid directional arrow C) such that the first reaction mixture 76 is transported by gravity to the sample read window 64 in the second corner 72, and the reaction cassette 40 is maintained in a stationary position. Any such detectable response provided by the first reaction mixture 76 can then be measured, and the remaining assay steps, if necessary, can be carried out subsequent thereto.

By way of example only and not by way of limitation, the detectable responses may be a total hemoglobin measurement where the liquid test sample is whole blood, for example, such as when performing an assay for the percent of glycated hemoglobin (HbA1c) in a whole blood sample, as well as a measurement of the total volume of the liquid reagent/buffer 75A present in the first reaction mixture 76.

With respect to the dye added to the oxidant on the node comprising the first solid reagent zone 65, the dye, in one non-limiting embodiment, has a known extinction coefficient at particular wavelengths or ranges of wavelengths of light. For instance, the dye may have a known extinction coefficient when interrogated at a wavelength of about 536 nanometers (the absorbance wavelength of hemoglobin-containing specimens) and within the infrared spectrum (from about 700 nanometers to about 900 nanometers). Ideally, the selected dye(s) should not cause interference with the absorbance measurement(s) associated with a patient's liquid test sample (for instance, whole blood); however, often times this is not the case. Accordingly, one aspect of the presently disclosed and/or claimed inventive concept(s) is to provide a method for accounting for and mitigating, if not eliminating, the effects of interference resulting from the at least one dye. When hemoglobin (including, without limitation, its varying forms, such as, by way of example, methemoglobin, hemoglobin Fe (II), methemoglobin Fe (III), and thiocyanomethemoglobin Fe (III)) is the analyte of interest to be measured via the conductance of one or more assays within the reaction cassette 40, the extinction coefficient of the at least one dye is preferably known at about 536 nanometers to correct for any interference introduced by the at least one dye that results in incorrect or incomplete absorbance and/or concentration readings of the hemoglobin (and its variants) present within the patient's liquid test sample.

Figure 4:
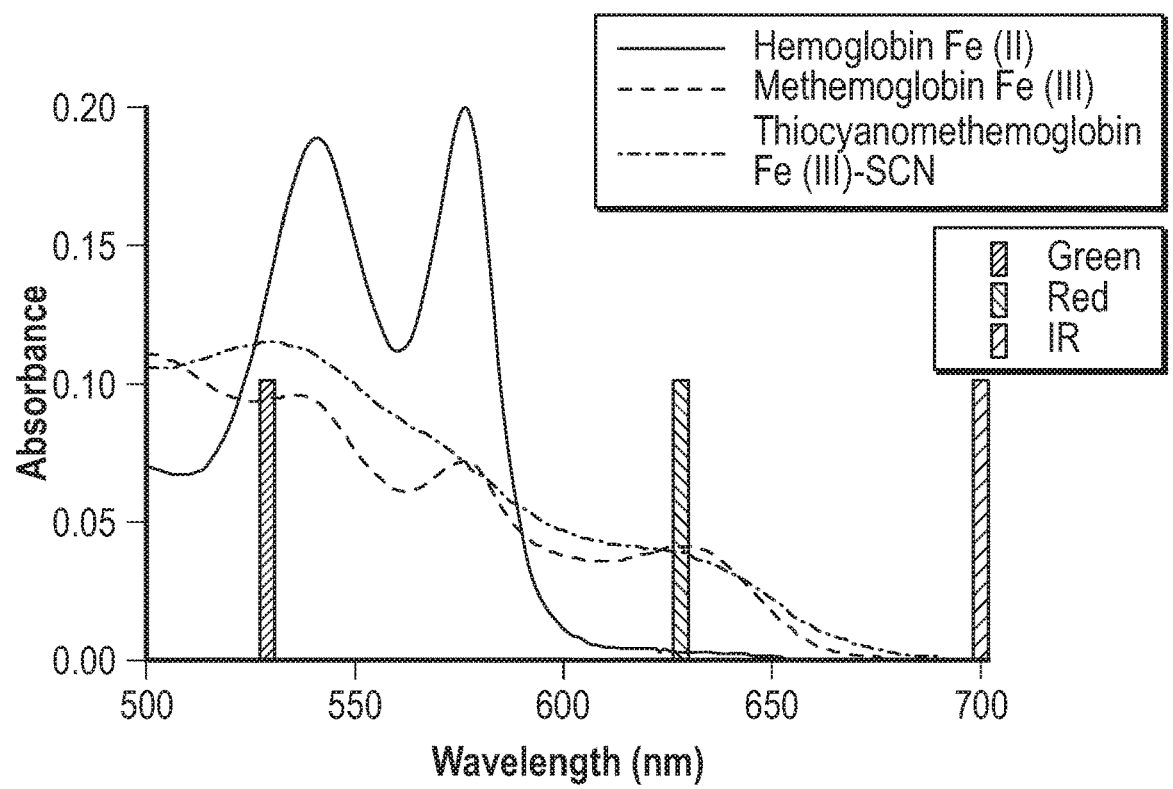
FIG. 4 is a graphical plot showing the spectrophotometric absorbance readings of hemoglobin and hemoglobin oxidized variants ranging from about 500 nanometers to about 690 nanometers.

As shown in FIG. 4, hemoglobin (and its variants, such as, for example, its oxidized variants formed as a result of the oxidation of hemoglobin caused by the combination of the patient's liquid test sample with the at least one oxidant, for instance, FeCN, and the at least one dye, for instance, NGB, at or on the node of the first reaction zone 65 containing such constituents) show spectrophotometric absorbance readings ranging from about 500 nanometers to about 690 nanometers. Depending on the level of precision needed when calculating the concentration of hemoglobin present in a patient's liquid test sample, the extinction coefficient of the at least one dye needs to be known at about 536 nanometers to correct for any interference caused by the at least one dye when measuring the concentration of hemoglobin. The absorbance(s) of the at least one dye (for instance, NGB) in the spectral range of from about 700 nanometers to about 900 nanometers can be used to calculate the at least one dye's contribution to interference to the absorbance reading for hemoglobin concentration at about 536 nanometers. However, a correction may not need to be performed if the contribution of the at least one dye (for instance, NGB) is relatively constant.

Figure 5:
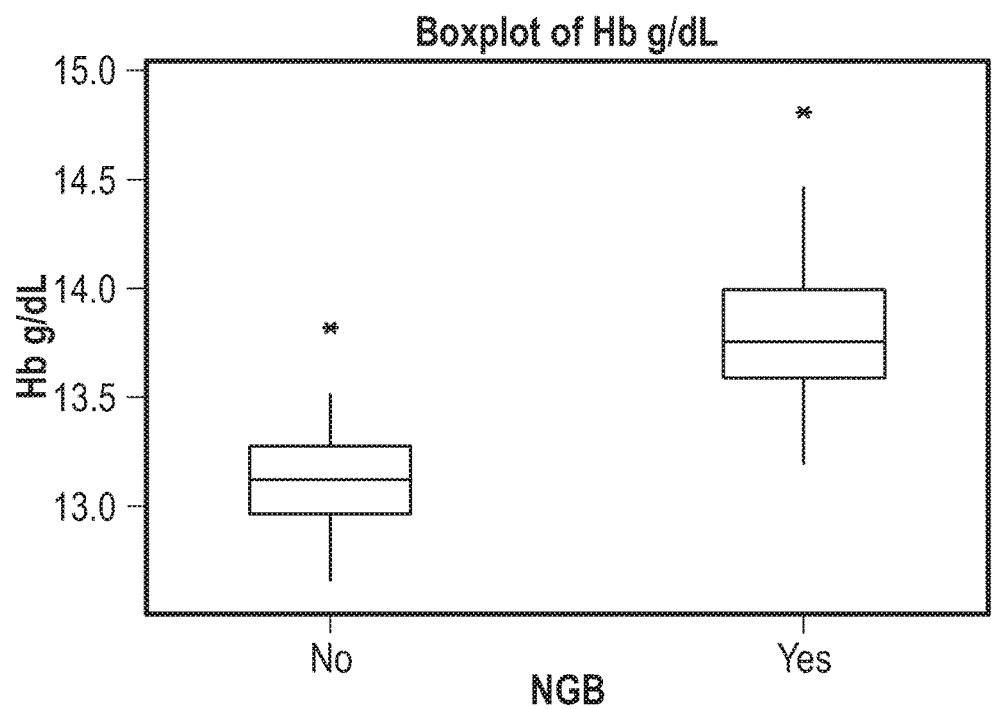
FIG. 5 is a boxplot graph showing the impact of NGB dye on the hemoglobin concentration read in accordance with the presently disclosed and/or claimed inventive concept(s).

Referring now to FIG. 5, shown therein is a boxplot graph showing the impact of NGB dye on the hemoglobin concentration read (for instance, in read window 64) in accordance with the presently disclosed and/or claimed inventive concept(s). FIG. 5 shows the difference in hemoglobin concentration read on a sample that does not contain NGB (left plot) and a sample that does contain NGB (right plot). When a correction is desired, the differences in hemoglobin concentration could be corrected by subtracting out the expected contribution of NGB or by simply utilizing the difference as background during normal calibration.

For correction via subtraction, for instance, an assay may be run and an absorbance value of NGB may be obtained at 725 nanometers (e.g., within the infrared spectrum). Accordingly, this absorbance at 725 nanometers can be used to estimate the NGB signal contribution at about 531 nanometers (within the range of spectral absorbance of hemoglobin) and the signal can be corrected for NGB interference via subtraction of absorbance measurements.

For correction via calibration, a predetermined amount of oxidant (for instance, by way of example, FeCN) is mixed with a predetermined amount of at least one dye (for instance, by way of example, NGB), such that the molarity (moles/L) of the at least one dye is, in one non-limiting example, about 5.69E-04. During calibration, the calibrators (for instance, the calibrators present within a commercial analyzer commonly known in the art) have assigned percent glycated hemoglobin (% HbA1c) values. As a result of this pre-assignment, % HbA1c is known and when the concentration of hemoglobin is read, the changes in agglutination absorbance are known.

Figure 6A:
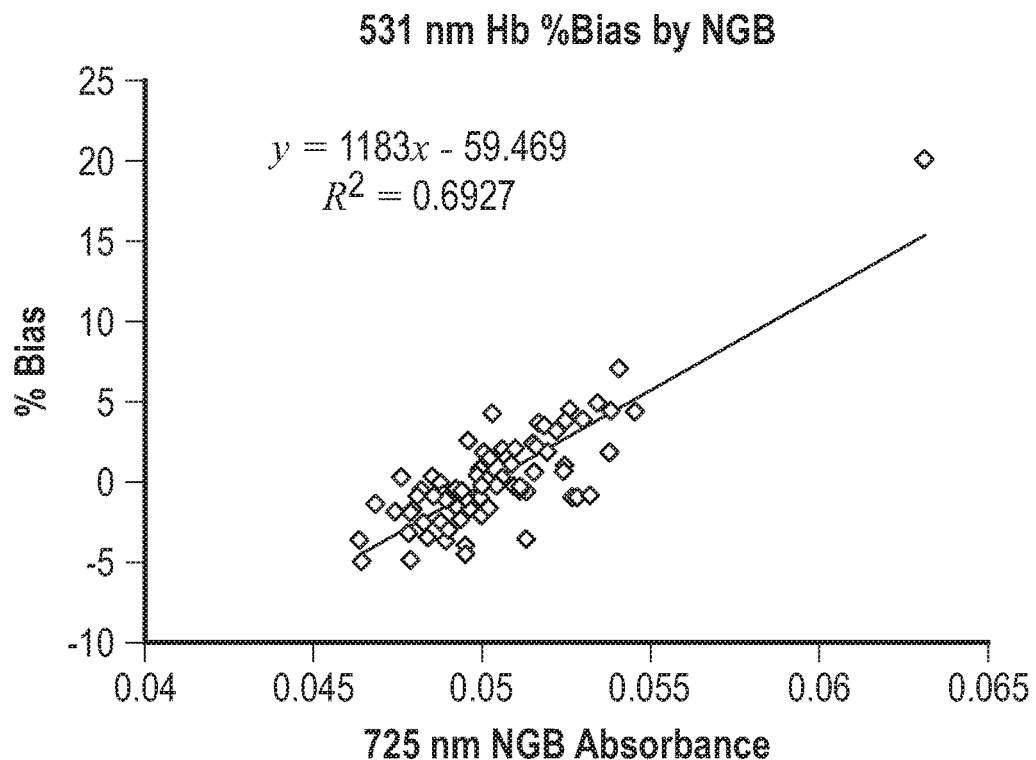
FIGS. 6A-6C are graphical plots showing the relationship between % bias and NGB absorbance in accordance with the presently disclosed and/or claimed inventive concept(s).
Figure 6B:
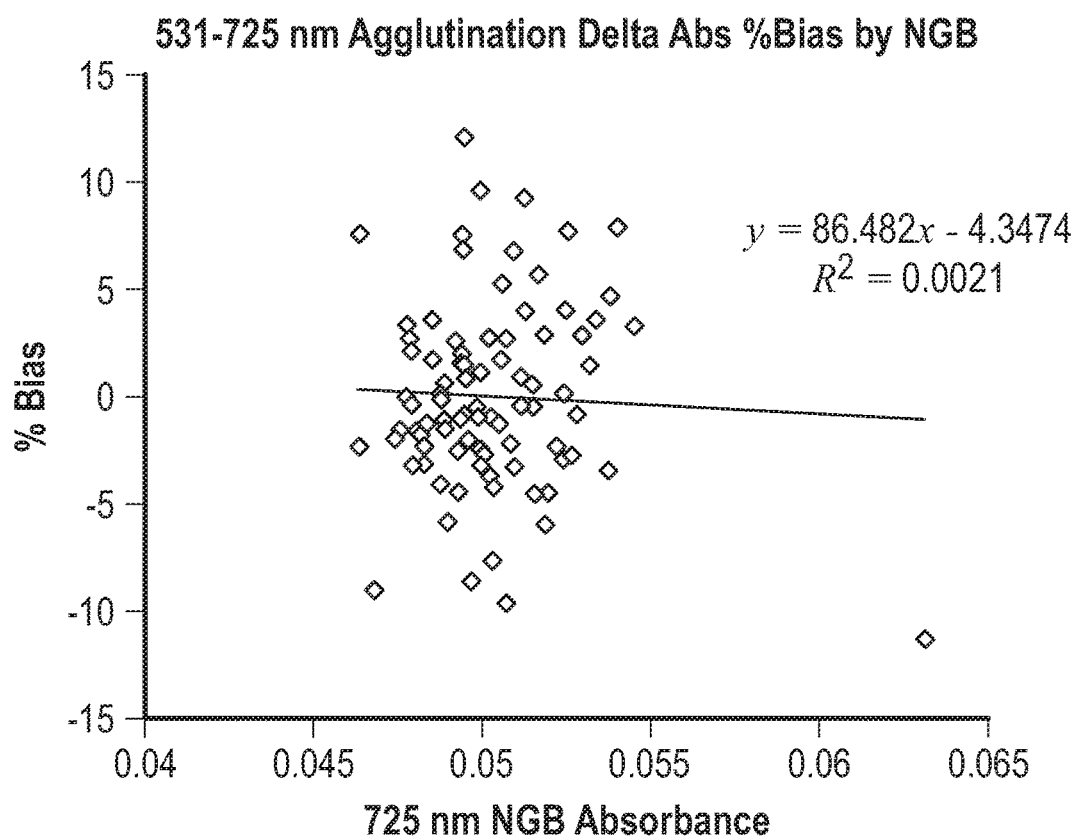
Figure 6C:
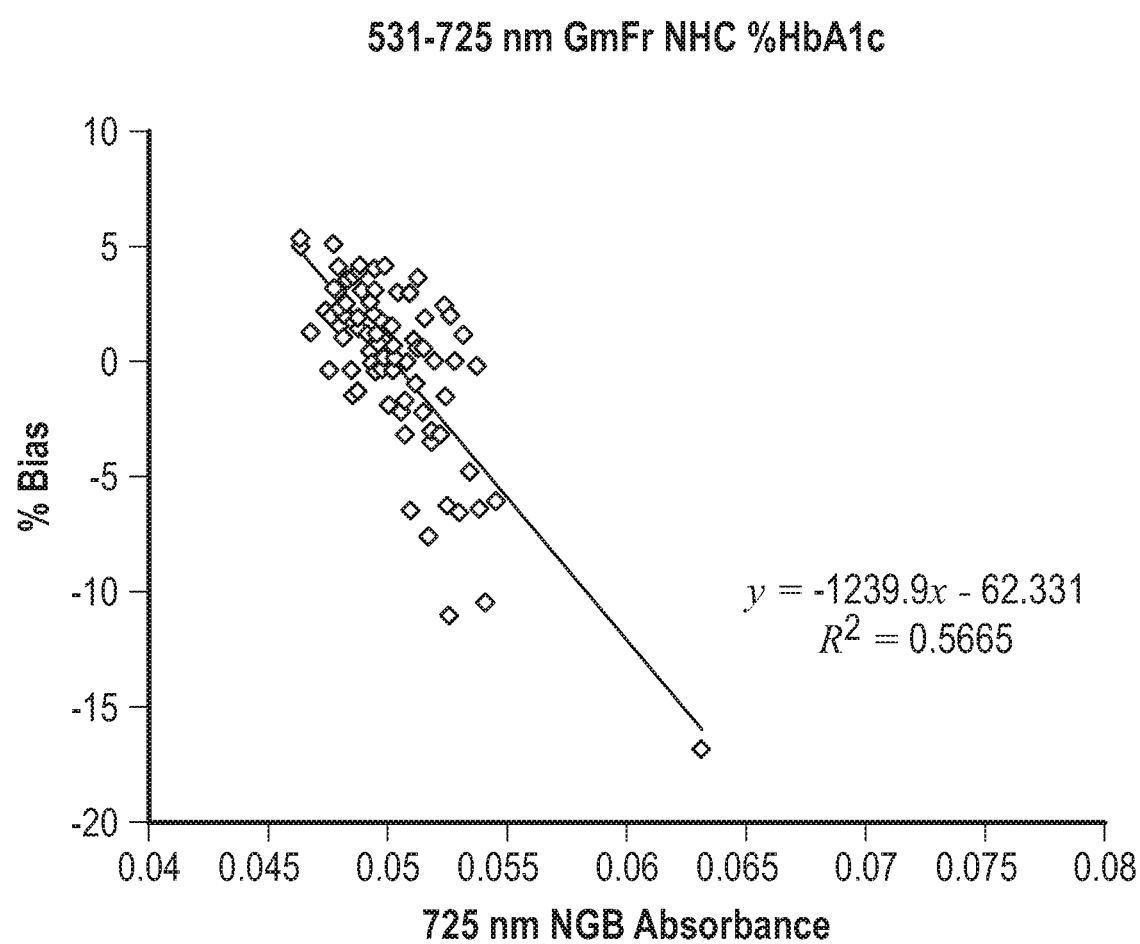

Referring now to FIGS. 6A-6C, shown therein are examples of the calculation of bias (for instance, measured as % bias which is defined as the specific bias of each measurement in a set against the mean value of the particular set) associated with particular sample measurements. When the concentration of the at least one dye (such as, by way of example only, NGB) is known and the volume and oxidation reagent (such as, by way of example only FeCN) is known, any difference in the chosen absorbance spectrum (for instance, by way of example only, 700-900 nanometers) will correlate to buffer volume (and thus bias).

As shown in FIG. 6A, when the buffer volume decreases, NGB increases as does the measured concentration of hemoglobin. When looking at agglutination kinetics (FIG. 6B), however, the correlation between bias and the concentration of NGB does not appear to exist. The final bias results (shown in FIG. 6C), however, significantly correlate to NGB absorbance—as the concentration of hemoglobin increases, the % of glycated hemoglobin drops. This relationship between % glycated hemoglobin and the concentration of hemoglobin is represented by Equation 1 below:

$$\% \text{ Hb1Ac} = (\mu M \text{ of Hb1Ac}/(10*\text{mmHb}))*100 \quad [1]$$

An exemplary correction of a 5.7% Hb1Ac sample is detailed in Table 1 below, which utilizes the slope-intercept formula of FIG. 6C for the calculation of % bias associated with the particular NGB absorbance. If the NGB absorbance obtained is 0.06, then, according to FIG. 6C, the bias to the true value is about 12.5%. In order to increase the value of the result by 12.5%, step 3 identified in Table 1 is utilized. The initial result of 5.7% Hb1Ac is multiplied by the needed correction coefficient thereby yielding a corrected value of 6.4125% Hb1Ac.

TABLE 1

Step By Step Correction of a 5.7% HbA1c Initial Result Sample

| Step | Description |
|---|---|
| 1 | Initial Result = 5.7% HbA1c |
| 2 | NGB Abs is 0.06 putting the bias at −12.5% |
| 3 | Needed Correction = (1 − ( −12.5/100 ) = 1.125 |
| 4 | Corrected Value = 5.7 * 1.125 ≈ 6.4% HbA1c |

Figure 7A:
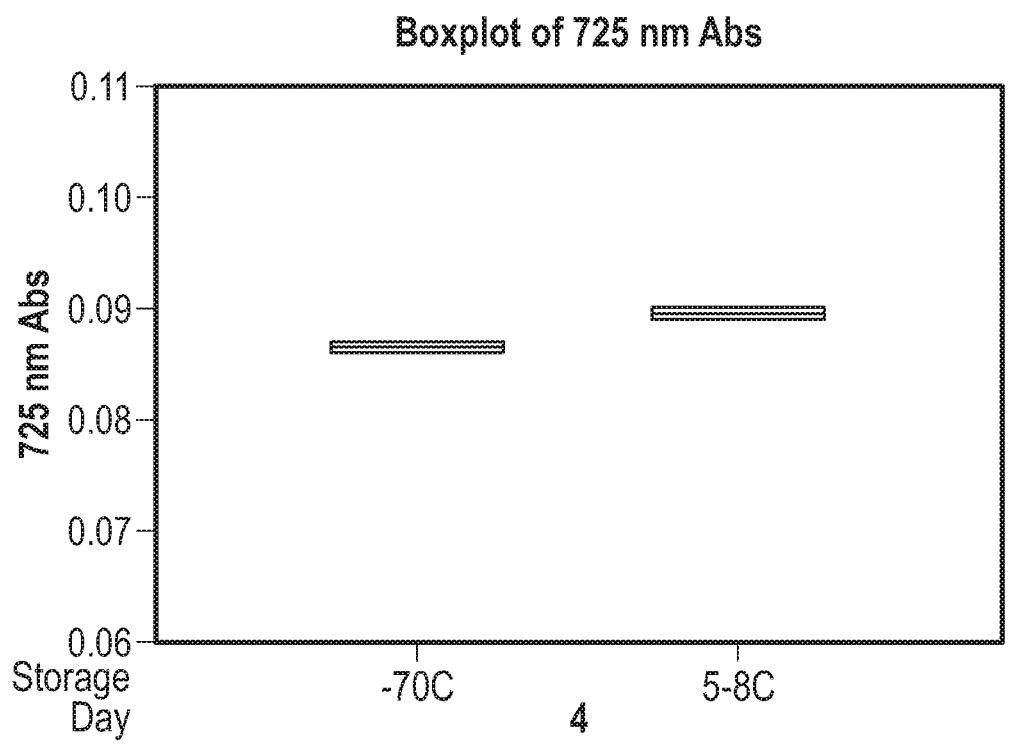
FIG. 7A-7B are graphical plots showing the stability of NGB stored with a FeCN oxidant when measured at an absorbance wavelength of about 725 nanometers on days 1 and 4 after NGB addition at both −70° C. and a range of from about 5-8° C.
Figure 7B:
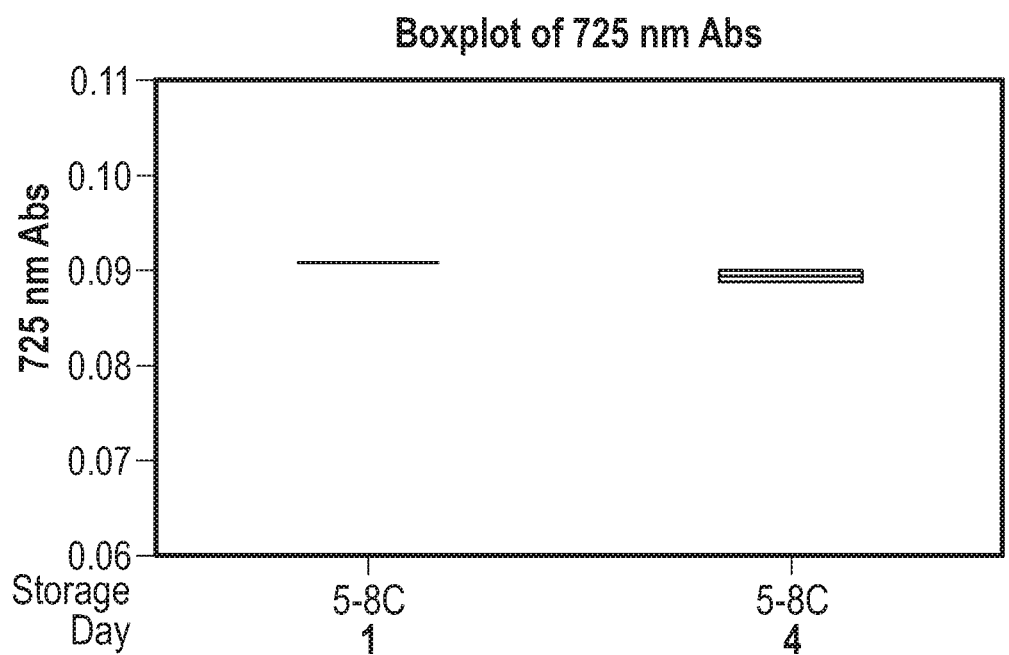

In certain non-limiting embodiments of the presently disclosed and/or claimed inventive concept(s), NGB is used as the at least one dye which is added to the oxidizing reagent (such as FeCN) due to NGB's low absorbance at 536 nanometers (a common absorbance wavelength of hemoglobin-containing specimens), high absorbance at 725 nanometers, and its high solubility in water. As shown in FIGS. 7A and 7B, when protected from light, NGB is stable when stored with FeCN when the absorbance is measured at 725 nanometers on days 1 and 4 after NGB addition at both −70° C. and a range of from about 5-8° C.

Figure 8:
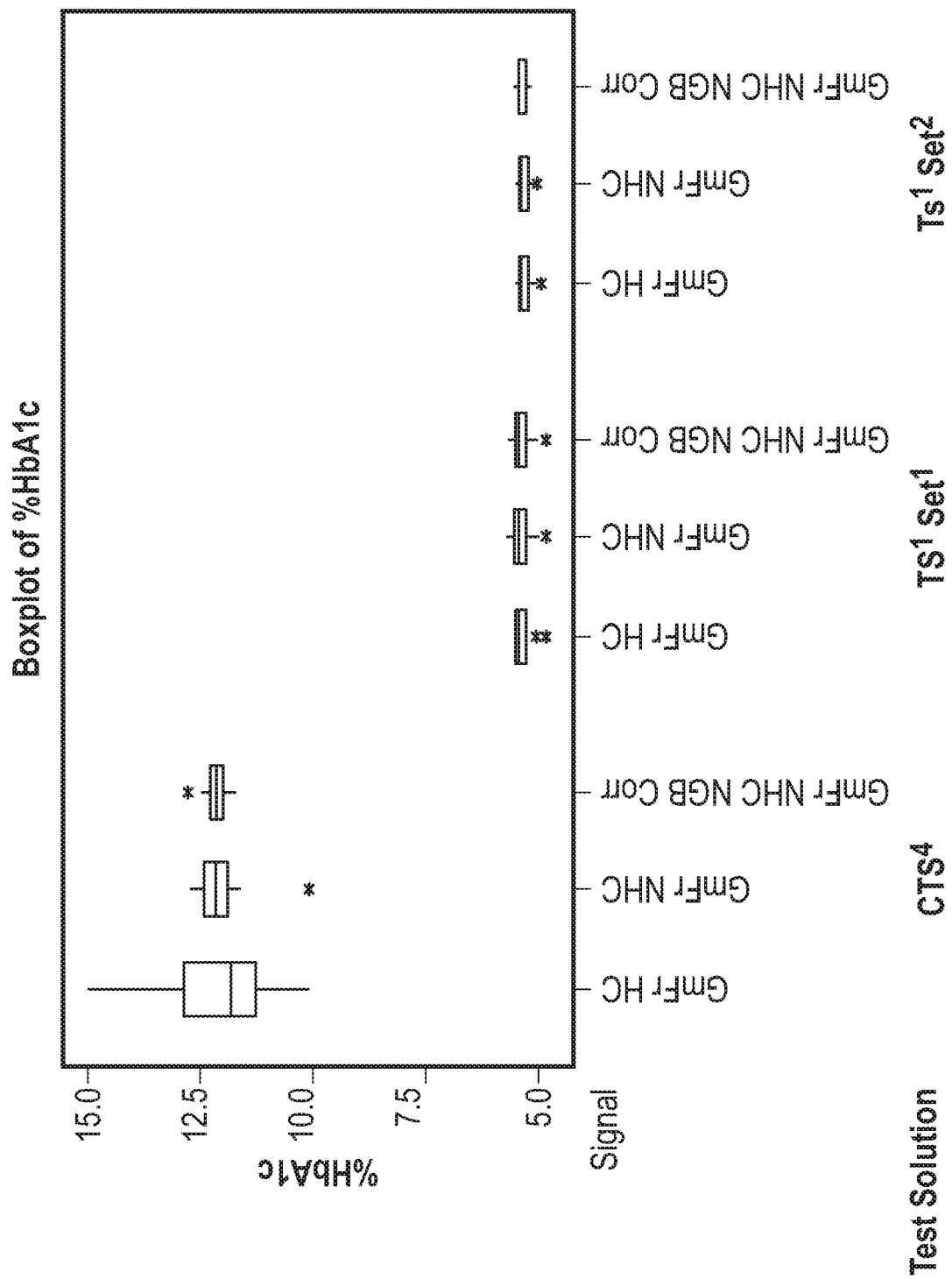
FIG. 8 is a boxplot graph showing the precision of % Hb1Ac calculations with and without the presence of NGB in accordance with the presently disclosed and/or claimed inventive concept(s).

Referring now to FIG. 8, shown therein is a boxplot showing the precision of % Hb1Ac calculations with and without the presence of NGB. When a Napthol Green B correction model is used for the data collected in FIG. 8 (represented in FIG. 8 by the term "NGB"), such derived correction is in accordance with the slope-intercept formula detailed in FIG. 6C. When each set detailed in FIG. 8 (represented as CTS4, TS1 Set 1, and TS1 Set 2) was run, the first three replicates (CTS4) were run normally (i.e., the flexible cover 71 was pulled at a normal and consistent speed). The middle three replicates (TS1 Set 1) had the flexible cover 71 removed quickly so as to generate a dataset that includes buffer loss imprecision. The last set of three replicates (TS1 Set 2) were again run normally. As shown in Table 2 below, when a correction model is used on the % Hb1Ac data collected in FIG. 8, the coefficient of variation (% CV) is reduced, thus improving the reliability and precision of the assay(s) performed. "GmFr" is a signal correction for agglutination that uses green and red wavelengths. "NHC" means that no hemoglobin correction model was used, while "HC" means that a hemoglobin correction model was used on the particular data collected.

TABLE 2

| | % Hb1Ac Precision With and Without the Use of NGB | | | | | | | | | |
|---|---|---|---|---|---|---|---|---|---|---|
| | GmFr HC | | GmFr NHC | | GmFr NHC NGB Corr Sample | | NHC NGB Difference | | HC NGB Difference | |
| | TS1 | CTS4 | TS1 | CTS4 | TS1 | CTS4 | TS1 | CTS4 | TS1 | CTS4 |
| % CV | 8.9 | 2.9 | 3.5 | 3.8 | 2.6 | 1.9 | 0.9 | 1.9 | 6.3 | 1.0 |

Non-limiting Examples of the Inventive Concept(S)

A method for detecting and correcting inaccurate concentrations of an analyte of interest present within a patient's liquid test sample, the method comprising the steps of: providing a housing for conducting at least one diagnostic assay, wherein the housing comprises: a reaction chamber for the conductance of one or more diagnostic assays, the reaction chamber further comprising at least one solid reagent zone, wherein at least one of the at least one solid reagent zone comprises: at least one dye, wherein the at least one dye produces at least two detectable responses when the at least one dye is mixed with at least one liquid reagent, wherein the at least two detectable responses produced by the at least one dye are measured at different wavelengths; and a liquid analytical reagent dispensing apparatus contained within the housing, the apparatus comprising: a container, wherein the container contains at least one liquid analytical reagent, the container being in fluid communication with the reaction chamber to thereby dispense the at least one liquid analytical reagent into the reaction chamber at a predetermined time; introducing the liquid test sample into the reaction chamber; introducing the at least one liquid analytical reagent from the dispensing apparatus into the reaction chamber, whereby the at least one liquid analytical reagent mixes with the liquid test sample and the at least one dye to thereby form a reaction mixture in the reaction chamber; measuring a first detectable response in the reaction mixture, wherein the first detectable response is measured at a first wavelength to obtain a first value; measuring a second detectable response in the reaction mixture, wherein the second detectable response is measured at a second wavelength to obtain a second value; and subtracting a value derived from the second value from the first value to obtain a corrected value, the corrected value corresponding to a corrected concentration of the analyte of interest present in the liquid test sample.

The method, wherein the liquid test sample is a volume of whole blood.

The method, wherein the volume of whole blood is in a range of from about 0.1 microliter to about 100 microliters.

The method, wherein the at least one solid reagent zone further comprises at least oxidant.

The method wherein the at least one oxidant comprises ferricyanide.

The method, wherein the at least one dye is selected from the group consisting of naphthol green B (NGB), 1,1',3,3,3',3'-hexamethylindotricarbocyanine iodide, 1,1'-diethyl-4,4'-carbocyanine iodide, manganese (II) pthalocyanine, silicon 2,3-napthalocyanine dichloride, 3,3'-diethylthiatricarbocyanine perchlorate, near infrared (NIR)-II dye carboxylic functionalized, and combinations thereof.

The method, wherein the at least one liquid analytical reagent comprises at least one buffer having a volume of about 600 microliters.

The method, wherein the first wavelength is about 536 nanometers and the first value is an absorbance measurement of the at least one buffer at said first wavelength.

The method, wherein the second wavelength is about 725 nanometers and the second value is an absorbance measurement of the at least one buffer at said second wavelength.

The method, wherein the analyte of interest is selected from the group consisting of total hemoglobin, glycated hemoglobin, and combinations thereof.

An improved analytical reaction kit for use in the conductance of at least one diagnostic assay on a patient's liquid test sample, comprising: a housing for conducting at least one diagnostic assay, wherein the housing comprises a reaction chamber for the conductance of one or more diagnostic assays, the reaction chamber further comprising at least one solid reagent zone, wherein at least one of the at least one solid reagent zone comprises: at least one dye, wherein the at least one dye produces at least two detectable responses when the at least one dye is mixed with at least one liquid reagent, wherein the at least two detectable responses produced by the at least one dye are measured at different wavelengths; and a liquid analytical reagent dispensing apparatus contained within the housing, the apparatus comprising: a container, wherein the container contains at least one liquid analytical reagent, the container being in fluid communication with the reaction chamber to thereby dispense the at least one liquid analytical reagent into the reaction chamber at a predetermined time.

The analytical reaction kit, wherein the liquid test sample is a volume of whole blood.

The analytical reaction kit, wherein the volume of whole blood is in a range of from about 0.1 microliter to about 100 microliters.

The analytical reaction kit, wherein the at least one solid reagent zone further comprises at least one oxidant.

The analytical reaction kit, wherein the at least one oxidant comprises ferricyanide.

The analytical reaction kit, wherein the at least one dye comprises a known absorbance in a spectral range of from about 700 nanometers to about 900 nanometers.

The analytical reaction kit, wherein the at least one dye is selected from the group consisting of naphthol green B (NGB), 1,1',3,3,3',3'-hexamethyllindotricarbocyanine iodide, 1,1'-diethyl-4,4'-carbocyanine iodide, manganese (II) pthalocyanine, silicon 2,3-napthalocyanine dichloride, 3,3'-diethylthiatricarbocyanine perchlorate, near infrared (NIR)-II dye carboxylic functionalized, and combinations thereof.

The reaction kit, wherein the at least one diagnostic assay comprises a glycated hemoglobin detection assay.

The reaction kit, wherein the at least one liquid analytical reagent comprises at least one buffer comprising a volume of about 600 microliters.

The analytical reaction kit, wherein the reaction chamber of the reaction cassette further comprises a sample read window.

As described herein, the presently disclosed and claimed inventive concept(s) relate to embodiments of a modified apparatus that dispenses at least one liquid reagent(s) and/or buffer for the conductance of at least one diagnostic assay, as well as kits and methods of use related thereto. More specifically, as described herein, the presently disclosed and/or claimed inventive concept(s) relate to non-limiting embodiments of a modified reaction cassette that comprises at least one dye for determining whether results obtained from the conductance of at least one diagnostic assay are biased, as well as kits and methods of use related thereto. Accordingly, the present disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A method for detecting a concentration of an analyte of interest present within a patient's liquid test sample, the method comprising the steps of:
   (A) providing a housing for conducting at least one diagnostic assay, wherein the housing comprises:
      a reaction chamber for the conductance of one or more diagnostic assays, the reaction chamber further comprising at least one solid reagent zone, wherein the at least one solid reagent zone comprises:
         at least one solid analytical reagent that specifically interacts or associates with the analyte of interest for detection of the analyte of interest; and
         at least one solid dye, wherein the at least one dye produces at least two detectable responses when the at least one dye is mixed with at least one liquid reagent, wherein the at least two detectable responses produced by the at least one dye are measured at different wavelengths, and wherein the at least one dye does not interact or associate with the analyte of interest; and
      a liquid analytical reagent dispensing apparatus contained within the housing, wherein the liquid analytical reagent dispensing apparatus contains at least one liquid analytical reagent and is in fluid communication with the reaction chamber to thereby dispense the at least one liquid analytical reagent into the reaction chamber at a predetermined time;
   (B) introducing the liquid test sample into the reaction chamber;
   (C) dispensing the at least one liquid analytical reagent from the dispensing apparatus into the reaction chamber, whereby the at least one liquid analytical reagent mixes with the liquid test sample and solubilizes the at least one solid analytical reagent and the at least one solid dye to thereby form a reaction mixture in the reaction chamber;
   (D) performing an analytical assay procedure using the solubilized at least one analytical reagent to determine a concentration of the analyte of interest present in the liquid test sample;
   (E) measuring a first detectable response in the reaction mixture for the at least one dye, wherein the first detectable response is measured at a first wavelength to obtain a first value;
   (F) measuring a second detectable response in the reaction mixture for the at least one dye, wherein the second detectable response is measured at a second wavelength to obtain a second value;
   (G) comparing the second value of (F) to an expected value to calculate buffer loss;
   (H) comparing the first and second values to determine if any interference contribution of the at least one dye is present in the concentration of the analyte of interest determined in step (D); and
   (I) calculating a corrected concentration of the analyte of interest present in the liquid test sample using the comparisons of steps (G) and (H) to thereby remove any interference contribution of the at least one dye and to correct for any inaccuracy or bias caused by loss of volume of the at least one liquid analytical reagent during the dispensing step.

2. The method of claim 1, wherein the liquid test sample is a volume of whole blood.

3. The method of claim 2, wherein the volume of whole blood is in a range of from about 0.1 microliter to about 100 microliters.

4. The method of claim 1, wherein the at least one solid reagent zone further comprises at least one oxidant.

5. The method of claim 4, wherein the at least one oxidant comprises ferricyanide.

6. The method of claim 1, wherein the at least one dye is selected from the group consisting of naphthol green B (NGB), 1,1',3,3,3',3'-hexamethyllindotricarbocyanine iodide, 1,1'-diethyl-4,4'-carbocyanine iodide, manganese (II) pthalocyanine, silicon 2,3-napthalocyanine dichloride, 3,3'-diethylthiatricarbocyanine perchlorate, near infrared (NIR)-II dye carboxylic functionalized, and combinations thereof.

7. The method of claim 1, wherein the at least one liquid analytical reagent comprises at least one buffer having a volume of about 600 microliters.

8. The method of claim 1, wherein the first wavelength is about 536 nanometers.

9. The method of claim 1, wherein the second wavelength is about 725 nanometers.

10. The method of claim 1, wherein the analyte of interest is selected from the group consisting of total hemoglobin, glycated hemoglobin, and combinations thereof.

11. An improved analytical reaction kit for use in the conductance of at least one diagnostic assay on a patient's liquid test sample, comprising:
   a housing for conducting at least one diagnostic assay, wherein the housing comprises a reaction chamber for the conductance of one or more diagnostic assays, the reaction chamber further comprising at least one solid reagent zone, wherein the at least one solid reagent zone comprises:
      at least one solid analytical reagent that specifically interacts or associates with the analyte of interest for detection of the analyte of interest; and
      at least one solid dye, wherein the at least one dye produces at least two detectable responses when the at least one dye is mixed with at least one liquid reagent, wherein the at least two detectable responses produced by the at least one dye are measured at different wavelengths, and wherein the at least one dye does not interact or associate with the analyte of interest; and a liquid analytical reagent dispensing apparatus contained within the housing, wherein the liquid analytical reagent dispensing apparatus contains at least one liquid analytical reagent and is in fluid communication with the reaction chamber to thereby dispense the at least one liquid analytical reagent into the reaction chamber at a predetermined time.

12. The analytical reaction kit of claim 11, wherein the liquid test sample is a volume of whole blood.

13. The analytical reaction kit of claim 12, wherein the volume of whole blood is in a range of from about 0.1 microliter to about 100 microliters.

14. The analytical reaction kit of claim 11, wherein the at least one solid reagent zone further comprises at least one oxidant.

15. The analytical reaction kit of claim 14, wherein the at least one oxidant comprises ferricyanide.

16. The analytical reaction kit of claim 11, wherein the at least one dye comprises a known absorbance in a spectral range of from about 700 nanometers to about 900 nanometers.

17. The analytical reaction kit of claim 16, wherein the at least one dye is selected from the group consisting of naphthol green B (NGB), 1,1',3,3,3',3'-hexamethyllindotricarbocyanine iodide, 1,1'-diethyl-4,4'-carbocyanine iodide, manganese (II) pthalocyanine, silicon 2,3-napthalocyanine dichloride, 3,3'-diethylthiatricarbocyanine perchlorate, near infrared (NIR)-II dye carboxylic functionalized, and combinations thereof.

18. The analytical reaction kit of claim 11, wherein the at least one diagnostic assay comprises a glycated hemoglobin detection assay.

19. The analytical reaction kit of claim 11, wherein the at least one liquid analytical reagent comprises at least one buffer comprising a volume of about 600 microliters.

20. The analytical reaction kit of claim 11, wherein the reaction chamber of the housing further comprises a sample read window.

* * * * *